United States Patent
Stauffer (10) Patent No.: US 6,920,793 B2
(45) Date of Patent: Jul. 26, 2005

(54) SYSTEMS AND APPARATUS FOR AIRBORNE ULTRASONIC TESTING OF PACKAGE AND CONTAINER SEALS

(75) Inventor: Anton Stauffer, Bedford, NY (US)

(73) Assignee: Packaging Technologies & Inspection LLC, Tuckahoe, NY (US)

(*) Notice: Subject to any disclaimer, the term of this patent is extended or adjusted under 35 U.S.C. 154(b) by 0 days.

(21) Appl. No.: 11/030,946

(22) Filed: Jan. 10, 2005

(65) Prior Publication Data

US 2005/0115324 A1 Jun. 2, 2005

Related U.S. Application Data

(63) Continuation of application No. 10/337,905, filed on Jan. 8, 2003, now Pat. No. 6,840,108.

(51) Int. Cl.[7] ............................................. G01N 29/00
(52) U.S. Cl. ........................ 73/630; 73/40.5 A; 73/52; 73/602
(58) Field of Search ........................... 73/630, 40.5 A, 73/52, 602, 45.4, 49.3, 588, 493, 600, 632, 73/598, 644

(56) References Cited

U.S. PATENT DOCUMENTS

| 3,290,922 A | 12/1966 | Thompson ..................... 73/52 |
| 3,384,767 A | 5/1968 | Arnold et al. ............... 310/366 |
| 3,608,715 A | 9/1971 | Snyder et al. ............... 209/590 |
| 4,333,028 A * | 6/1982 | Panton ........................ 310/326 |
| 4,821,573 A | 4/1989 | Nagata et al. ................ 73/597 |
| 4,864,848 A | 9/1989 | Irvine ......................... 73/45.4 |
| 5,319,956 A * | 6/1994 | Bogle et al. ............. 73/40.5 A |
| 5,359,895 A * | 11/1994 | Isenberg et al. .............. 73/582 |
| 5,372,042 A * | 12/1994 | Jarman et al. ................ 73/588 |
| 5,408,867 A | 4/1995 | Kunze et al. ............. 73/405 A |
| 5,821,424 A | 10/1998 | Rodriguez .................... 73/657 |
| 5,824,908 A * | 10/1998 | Schindel et al. .............. 73/632 |
| 5,880,359 A * | 3/1999 | Kono et al. .................. 73/49.3 |
| 6,009,756 A * | 1/2000 | Willems et al. ............... 73/643 |
| 6,014,891 A * | 1/2000 | Kirks ............................ 73/40 |
| 6,311,573 B1 | 11/2001 | Bhardwaj .................. 73/886.5 |
| 6,343,510 B1 | 2/2002 | Neeson et al. ................ 73/602 |
| 6,739,188 B1 * | 5/2004 | Prause ......................... 73/305 |
| 6,840,108 B2 * | 1/2005 | Stauffer ....................... 73/630 |

* cited by examiner

Primary Examiner—Hezron Williams
Assistant Examiner—Jacques M. Saint-Surin
(74) Attorney, Agent, or Firm—Dowell & Dowell, P.C.

(57) ABSTRACT

Systems and devices for testing or inspecting the integrity of package closure seals using contact and non-contact ultrasonic systems wherein a relative movement is created between a package seal and at least one ultrasonic transmitting transducer and at least one receiving transducer such that ultrasonic energy is focused so as to be transmitted toward and along a length of the seal from the transmitting transducer to the receiving transducer in a gaseous environment to thereby monitor energy signals which are analyzed to provide an indication of the seal integrity.

18 Claims, 12 Drawing Sheets

SYSTEMS AND APPARATUS FOR AIRBORNE ULTRASONIC TESTING OF PACKAGE AND CONTAINER SEALS

CROSS REFERENCE TO RELATED APPLICATIONS

This application is a continuation of U.S. patent application Ser. No. 10/337,905, filed Jan. 8, 2003, now U.S. Pat. No. 6,840,108, in the name of the same inventor.

BACKGROUND OF THE INVENTION

1. Field of the Invention

This invention is generally directed to systems and devices for integrity testing of seals associated with various packaging or containers and more specifically to a method and system for utilizing airborne or a combination of airborne and contact ultrasonic energy which is transmitted through a gaseous medium, such as air, to a seal from a transmitting transducer. A receiving transducer receives energy which either passes through the seal or is reflected therefrom and supplies signals to an analyzer or computer which provides output with respect to the seal integrity.

2. Brief Description of the Related Art

The non-contact, non-destructive and non-invasive inspection of the integrity of seals used in the packaging industry, and especially those used in packaging food, medical devices and pharmaceuticals, is becoming increasingly more important to ensure that the contents of packaged products remain suitable for use to thereby protect the health and welfare of consumers. In this respect, the industry provides for selectively testing of different product packaging including flexible pouches, trays, cups, blister packs, bottles and the like to ensure that the seals associated with such packages are free of faults or flaws. Such faults may be voids in a seal, inclusion of contaminants along a seal or closure, uneven and marginal heat seals, seals of insufficient size or width, delaminations in areas of a seal, and other seal characteristics associated with bonded materials utilized in the packaging industry.

There are numerous types of container filling and sealing machines currently used in the packaging industry. For example, vertical pouch filling and sealing machines are utilized to fill products through an opening in a top of the pouch afterwhich the pouch is sealed, cut and dropped onto a take away conveyor. Periodic or sequence testing of the seals is required to ensure that packages are free of contamination or faults.

Horizontal filling and sealing machines are used to either continuously move or periodically index packages which are filled from the top afterwhich a heat seal is provided using stationary or moving heat sealing jaws. The jaws may be associated with a heat sealing roller system. Seal testing is performed after sealing.

Certain type of pouches incorporate zipper or interlocking type closures which may be located adjacent to a heat seal. In order to prevent leakage, a zipper component on either side of the pouch is sealed by pressure and heat.

Form filled seal machines form a lower part of a package into a cavity and then load and fill a product into the package cavity and then seal a top layer onto the lower cavity or tray. This process is typically done in an indexing motion from one to several stations along a conveyor. The shape of the tray may be in any form, however, most are rectangular, square or round.

Regardless of the type of product filling and sealing machines used, inspection of packages following filling and sealing is critical to ensure the integrity of the seals and thus the suitability of the packaged product for later use or consumption. Often, because packages are filled at high speed under critical conditions, a product may contaminate the area of a seal and thus interfere with an effective seal. Further, sealing tools can become contaminated, misadjusted or worn and can lead to the formation of bad or faulty seals during the packaging sealing process. In view of the foregoing, it is necessary to provide a method for inspecting and determining the integrity of packaging seals before product is shipped to consumers.

There are currently and in the industry a number of methods and devices for testing the integrity of seals associated with packages having different types of closures. The most basic testing procedure is through manual inspection of packaging, either visually, by touch, feel or destructive means. Manual inspection is suitable to determine obvious problems associated with packaging, such as a missing or partially applied lid, a separated seal, a ruptured or damaged container or closure and the like. Manual inspection, however, is not efficient, provides no variable data and is not effective to determine seal characteristics such as contaminations, voids in seals, delamination of seal layers, microholes or defects in a seal and like. To reduce costs while providing greater effectiveness in inspecting package seals, automated procedures and systems have been developed to inspect or test seals.

Such automated testing procedures have included the use of devices for applying pressure to packages which are carried along a conveyor. The degree of deflection of a package, or the amount of recovery a lid or wall of a package, after pressure is applied, is measured to determine whether or not leaks are present in either the packaging materials or in the seals associated therewith. Other types of physical tests include measuring package weight gain or loss, monitoring lid or closure deflection to determine if proper internal pressure is obtained and maintained in a package, the use of tracer gases such as a carbon dioxide, oxygen and helium, and electrical conductivity.

Other types of leak testing systems incorporate vacuum sources in differential and absolute pressure sensory systems. Packages are placed within chambers and vacuums are applied such as to create a differential pressure between an interior of a package and the surrounding vacuum chamber. Pressures within the testing chambers can be monitored so as to determine if there are changes in pressure after vacuums or partial vacuums are applied to thereby give an indication of a faulty seal or leak.

In U.S. Pat. No. 5,513,516 to Stauffer, A Method And Apparatus For Testing A Container System is disclosed which incorporates a vacuum chamber in which a flexible or semi-flexible package is cooperatively received. A flexible wall or membrane is provided within the testing chamber and designed to provide a sealing surface against a wall of the container. The use of the flexible wall or membrane allows inspection of packaging formed of gas permeable materials to be tested such that, during the testing process, pressure differentials are only due to leaks along the package seals, and not the packaging material.

Some of the problems associated with prior art pressure type testing chambers for use in the packaging industry to ensure the integrity of packaging seals is that the packages must be placed within a supporting chamber, afterwhich a change is made to the atmosphere surrounding the package seal. In instances where pressure is applied by mechanical force, leaks can be plugged or covered and contamination can occur to packages as well as cross-contamination between packages. Further, the number of steps necessary to complete a seal test limits the effective number of containers or packages which can be tested or inspected at any given period of time and potential leaks, plugged leaks or weak seals are not detectable.

A further type of automated and testing system uses ultrasonic energy which is directed through a package seal in a liquid medium, such as water. Sealed containers are placed in a testing apparatus where a liquid is used to ultrasonically couple an ultrasonic transmitter array and a receiver array to the container rim. Using such a system, the liquid must be introduced around the seal in order to allow ultrasonic energy to be effectively transmitted through the seal and be detected by the receiver array. Thereafter, the liquid must be drained off and the package removed from the apparatus. Because of the requirement for a liquid environment, such ultrasonic systems are considered destructive in most cases and have not proven to be efficient and adequate for testing with respect to many container seals.

One of the essential features of any testing method and apparatus is that it must be economical to the manufacturer to use so that the cost of products are not increased, such as by limiting production due to slow testing procedures. In light of the foregoing, there remains a need to provide an apparatus and procedure for testing package seals which incorporates testing procedures which facilitate the manner in which package seals can be inspected to ensure their integrity and wherein such testing procedures and apparatus can be used efficiently so that products can be tested rapidly along a product filling line without adversely effecting the overall economics of the packaging system.

SUMMARY OF THE INVENTION

The present invention is directed to methods and devices for inspecting package seals utilizing both contact and non-contact ultrasonic energy systems which include at least one ultrasonic transmitting transducer and one ultrasonic receiving transducer, which may, in some instances be the same transducer, which are operable in a gaseous environment, such as under ambient conditions within a product packaging and/or sealing facility. Following the filling and sealing of a package or container, which may be of any of the types previously described, as well as others, the seal of the package is directly exposed to ultrasonic energy which is passed through it, or reflected from it, and along the length of the seal from the transmitting transducer such that the ultrasonic energy is received by the receiving transducer. The receiving transducer uses the energy received to produce signals which are analyzed to provide an indication of the integrity of the seal. In some embodiments, the package or container may remain stationary and a plurality of airborne ultrasonic transmitting transducers may be aligned along the length of the seal, regardless of its shape, with a plurality of receiving transducers used to measure the energy passing through the seal or reflected from the seal. In other embodiments, one or more transmitting transducers may be movably mounted relative to a stationary product container so that the transducers are moved to transmit energy along the length of a seal and wherein one or more receiving transducers are simultaneously moved or concurrently moved with the transmitting transducer or transducers to receive ultrasonic energy in order to produce the signals which give an indication of the seal integrity.

The methods of the invention may be used to effectively determine the integrity of not only heat seals but also glued or otherwise welded type seals utilized in the container or packaging industries. The transducers normally operate in frequency ranges of 100 KHZ to 5 MHZ. The materials to be joined can be any type of single or multi-layer plastic films, papers, aluminum foils and composite material structures, or combinations thereof.

In some embodiments, the energy from the ultrasonic transmitting transducer is focused to a defined shape relative to a seal in order to prevent the passage of ultrasonic energy around an edge of a package, especially where the edge of the package is spaced closely adjacent to the seal. This prevents any wrap around ultrasonic energy from adversely effecting the results detected by a receiving transducer which is spaced on an opposite side of the seal which could give a false indication of the integrity of the seal being tested. Some focusing devices may be barriers through which ultrasonic energy is transmitted or may be reflectors which concentrate the ultrasonic energy upon reflection from a predetermined surface toward and through a container seal.

In some embodiments of the invention, the edge of a package adjacent a seal may be passed through a guide such that the seal moves along a fixed path so as to pass between one or more fixed transmitting transducers and one or more receiving transducers.

In yet other embodiments, in order to prevent the stray or wrapped ultrasonic energy from effecting the readings of a receiving transducer, an edge of a package adjacent to a seal being tested may be screened or abutted by a shield member which, in some embodiments, may be resiliently mounted such that the shield rides along the edge of the package adjacent to the seal during seal testing. Such shields may be formed of rollers or wheels which track along an edge of a package.

The methods and systems of the present invention are specifically designed to permit ultrasonic testing in gaseous environments such as in ambient air conditions. In some embodiments, both the transmitting and the receiving transducers will be spaced at a predetermined distance from a package seal such that the ultrasonic energy is transmitted through a gaseous median to the seal. Much of the ultrasonic energy will be reflected from the seal, such as at areas between laminates of the seal, with only a small portion passing through the seal to the receiving transducer. In other embodiments, either the transmitting transducer or the receiving transducer may be in contact with a portion of the package adjacent to the seal during the seal inspection.

In yet a further embodiment of the present invention, the transmitting transducer and the receiving transducer may be positioned on the same side of a package seal being inspected such that ultrasonic energy is reflected off the seal area or off the laminates forming the seal from the transmitting receiver to the receiving transducer. In some other embodiments, the transmitting receiver may be electrically controlled such as to function as both a transmitting and a receiving transducer such that ultrasonic energy reflected from the seal area is received by the transmitting transducer.

In yet a further embodiment of the present invention, either the transmitting transducer or the receiving transducer may be moveable relative to a seal area, such as by forming the transducer in a configuration of a wheel which can rotate along the length of the seal with the wheel transducer being in contact with the package adjacent to the seal during seal inspection.

Using the method and systems of the present invention, inspection of preformed pouches, packages, trays, cups, bottles and other containers which are filled and sealed individually, can be accomplished at speeds up to or exceeding 200 to 500 units per minute.

The system of the present invention may also be used with proprietary self-learn algorithm software in combination with digital processors or computers which process initially received signals from a receiving transducer in order to continuously update information with regard to seal integrity. Preliminary setting of an analyzing computer or digital signal processor can be accomplished by passing a plurality good samples between the transmitting and receiving transducers and allowing the analyzer to detect and effectively learn the limits defined by good seals. In a like manner, seals having known defects, either by way of delamination, holes or openings in seal areas, insufficient seal widths, contaminated areas and the like can be passed between the transmitting and receiving transducers with the seals being analyzed so that the computer effectively creates data files for specifically identifying a type of seal flaw which may be encountered during testing. The systems for accomplishing such ultrasonic testing and proprietary self-learn algorithm procedures are disclosed in U.S. Pat. No. 6,343,510 to Neeson et al., the contents of which are incorporated entirely herein by reference and U.S. Pat. No. 6,311,573 to Bhardwaj, the contents of which are also incorporated in their entirety herein.

BRIEF DESCRIPTION OF THE DRAWINGS

A better understanding of the invention will be had with respect to the accompanying drawings wherein.

DESCRIPTION OF PREFERRED EMBODIMENTS

With continued reference to the drawing figures. The present invention will be described with respect to the use of both contact and non-contact airborne ultrasonic transducers to test or inspect the effectiveness or integrity of seals associated with numerous types of product packaging. The system and method utilized in the present invention can be used to test different product packaging including flexible pouches, formed trays, cups, blister packaging, plastic bottles, Tyvek™ containers and the like. For purposes of illustration, only some types of containers or packages will be described with reference to the drawing figures.

Packages or containers which can be inspected utilizing the systems and method of the present invention may be formed of many of a plurality of materials or composites including such materials as plastic films, laminates, papers, metal foils and the like. The seals may be formed by substantially any process including adhesive, welding, heat and pressure sealing and the like.

Figures 1, 2:
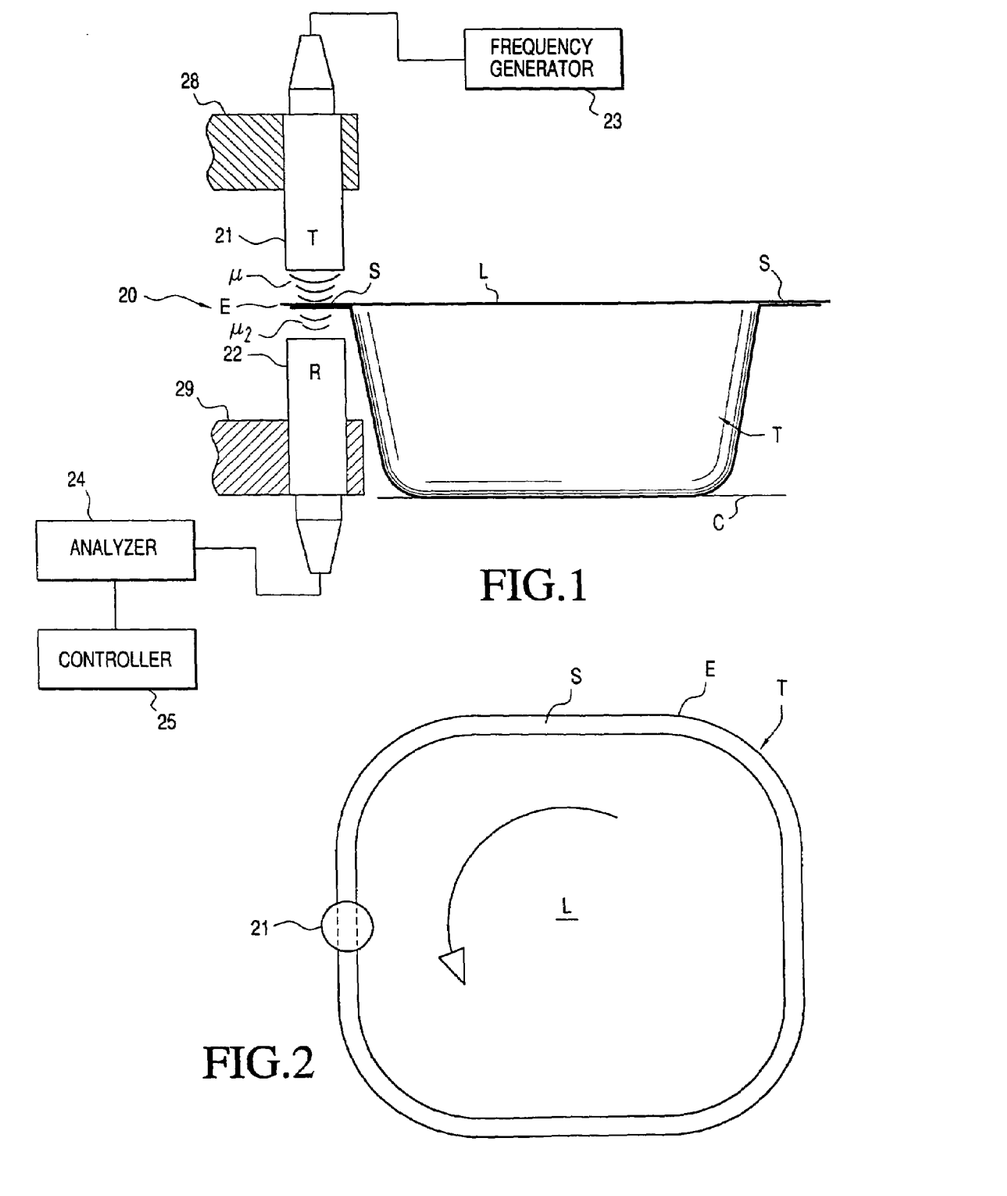
FIG. 1 is a partial side illustrational view showing a system of the present invention wherein a package in a form of sealed tray is tested.
FIG. 2 is a top plan view of the system of FIG. 1 showing movement of the package relative to the testing system.

A first embodiment of non-contact ultrasonic testing system where ultrasonic energy is passed through a seal of a container in a gaseous environment is shown in FIG. 1 at 20. The system includes at least one ultrasonic energy transmitting transducer 21 and at least one receiving transducer 22. The transmitting transducer and receiving transducer are aligned relative to a seal area "S" adjacent an edge "E" of the package, such as a tray "T", and both transducers are spaced in non-contacting relationship from the package or tray. The transducers are axially aligned with respect to one another so that ultrasonic energy "U" transmitted from the transmitting transducer 21 passes through the seal "S" after which energy "U2" is received by the receiving transducer 22. The transmitting transducer receives energy from a frequency generator 23. The receiving transducer develops a signal which is passed by way of electrical connection to a computer analyzer 24 wherein the received signal is analyzed in order to determine the integrity of the seal "S". Information from the analyzer can be used to provide input to a controller 25 such that a conveying line "C" on which the tray is carried can be controlled. If a flaw or defect in a seal is detected, the tray can be ejected from the product packaging line. In the embodiment shown, the transmitting transducer 21 is fixedly mounted to a support 28 while the receiving transducer is fixedly mounted to a support 29. This on-line inspection is done in linear-scan mode (L-Scan) emitting and analyzing signals as the seal passes between the transducers. Alternatively, one can analyze an entire heat seal with the C-Scan mode, which represents a micro acoustic image of multiple L-Scans done in a X-Y scan motion. The ultrasonic signals are converted into a color chart, representing a digital image of the seal area.

During the ultrasonic testing, the ultrasonic waves will be primarily reflected at the interface of the different material or laminates from which the package seal is formed. The reflected energy is greater than the amount of energy which passes through the seal. Therefore, a good seal allows only a very small portion of the transmitted energy to be received by the receiving transducer, with most of the energy being reflected from the surface of the container and from the interfaces of the layers of the different materials forming the seal, such as aluminum foils and plastic or paper layers. If the seal has delaminations, inclusions of air are other foreign materials therein, there is created additional interfaces that function as reflective barriers for the ultrasonic waves such that energy received by the receiving transducer will drop more than would be anticipated with a good seal.

In those instances wherein two portions or laminates of a seal are not appropriately aligned after sealing, the missing layer of the seal would create less of a barrier to the ultrasonic waves passing therethrough such that a signal at the receiving transducer would be increased.

Figure 3A:
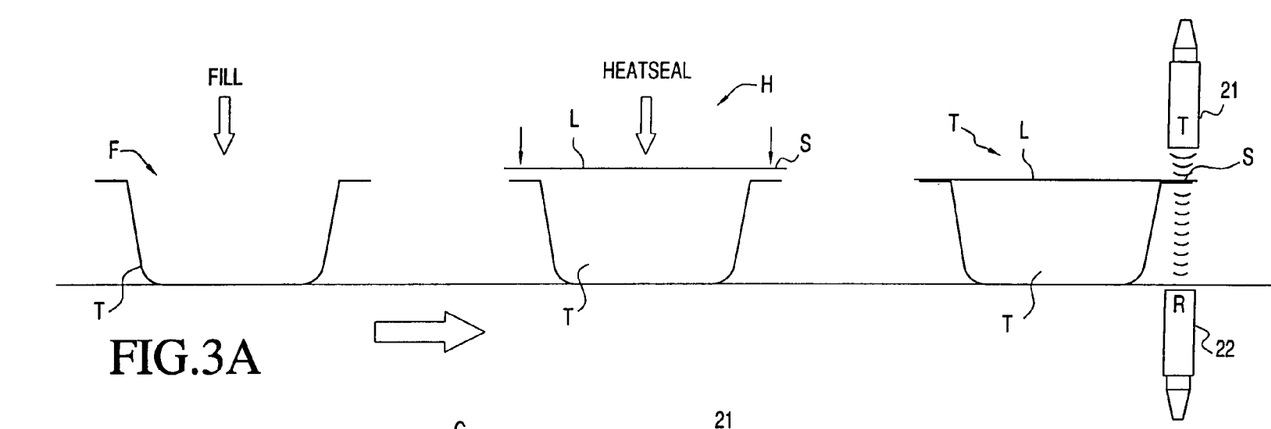
FIG. 3A is an illustrational view of the package of FIG. 1 being advanced between a filling, heat sealing and inspection station in accordance with the teachings of the present invention.

After a product has been filled withing the tray "T" and a closure or lid "L" applied thereto, the package or container passes through an appropriate sealing device which provides a seal adjacent the peripheral edge "E", as shown in FIG. 3A. The package then passes by way of the conveyor "C" to the testing station 20 wherein the seal is aligned between the transmitting transducer 21 and the receiving transducer 22.

With specific reference to FIG. 2, to test the entire length of the seal, the tray may be rotated relative to the transmitting transducer and receiving transducer, as is illustrated by the arrow in the figure such that the entire seal area "S" is tested by the passage of ultrasonic energy through a gaseous medium, such as air, which surrounds the seal and such that the entire length of the seal is analyzed to ensure that there are no flaws. In this embodiment, the conveyor "C" would include a rotatable section which would be indexed in the manner as shown by the arrow in FIG. 2 when the tray is aligned within the testing station 20, as shown in FIG. 1.

As opposed to moving the tray relative to the testing transducers, it is also possible that the transducers may be mounted on movable supports as opposed to fixed supports. In this event, the transmitting transducer and the receiving transducer would be moved relative to the seal "S" of the tray "T" and about is full periphery.

In addition to the foregoing, as opposed to using only a single set of transmitting and receiving transducers, a plurality of such transducers may be positioned around the periphery of the seal area in order to further facilitate the testing procedure and to reduce the time necessary to fully analyze the full length of a seal.

The energy transmitted from the transducer 21 generally is in the range from 100 KHZ to 5 MHZ. A preferred transducer system operable in a gaseous or airborne environment is disclosed in U.S. Pat. No. 6,311,573 to Bhardwaj, the contents of which are incorporated, in their entirety, herein by reference. The manner in which the analyzer is used to provide an indication of the integrity of the seal is generally described with respect to the testing system disclosed in U.S. Pat. No. 6,343,510 to Neeson et al., the contents of which are also incorporated, in their entirety, herein by reference.

One of the specific benefits of utilizing the analyzer system in the airborne contact or non-contact ultrasonic inspection systems is that the analyzer may be educated by passing seals of known integrity through the testing systems. By allowing the analyzer to obtain signals which are known to be good, the analyzer develops a data base of signals which are indicative of an effective seal. Likewise, by testing seals having various known defects and depending on the type of package seal, the analyzer's database can be keyed so as to effectively recognize what type of defect is present in a seal. By way of example, by testing a seal having a known delamination, in a laminated type product, the analyzer will know what types of signals are reflective of the specific delamination. Further, if a delamination is detected during a testing procedure, it will not only be possible to recognize the defect, but it is also possible to pinpoint the exact area of the defect.

With specific reference to FIG. 3A, a conveying system for the test system shown in FIGS. 1 and 2 is disclosed. The illustration shows a tray "T" being filled at a filling station "F" and then passing by way of conveyor "C" to the heat seal station "H" where the lid "L" is applied and sealed. Thereafter, the container tray "T" is passed between the transmitting and receiving transducers, 21 and 22.

Figure 3B:
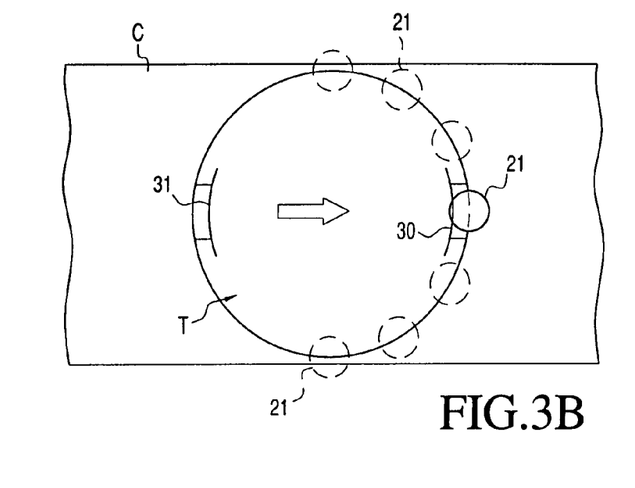
FIG. 3B is a top plan view of a modification of the testing system of the present invention.

In FIG. 3B, only a leading edge 30 and lagging edge 31 or zones of the seal are tested as the conveyor moves linearly past the transducers. Testing of only a portion of the seal, however, is not preferred in most testing procedures. In this embodiment, as opposed to only testing a segment of the seals, a plurality of spaced transmitting and receiving transducers may be positioned, as shown in dotted line, about portions of the container in order to ensure the entire length of the seal is tested.

Figure 4:
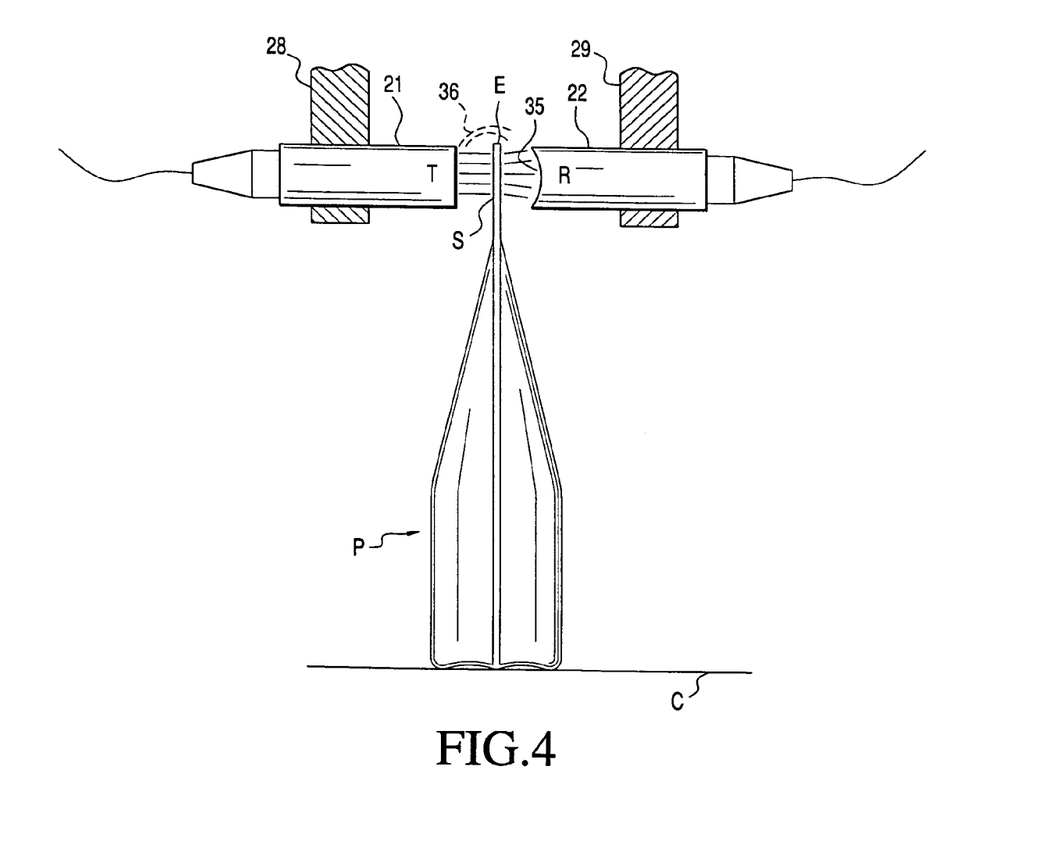
FIG. 4 is a modified embodiment similar to that disclosed in FIG. 1.

With specific reference to FIG. 4, a filled and sealed container in a form of a pouch "P" is disclosed which is carried by the conveyor "C". The pouch includes an upper sealed area "S" which passes between the transmitting transducer 21 and the receiving transducer 22 which are aligned so that ultrasonic energy from the transmitting transducer is directed to the receiving transducer. In this embodiment, either one of the transducers may include a structure which serves to more directly focus the ultrasonic energy in a definable form. This is shown by the concave face 35 of the receiving transducer 22. A like directing or focusing can be provided by the transmitting transducer with a similar configuration.

One of the potential problems utilizing non-contact airborne ultrasonic energy for testing is that it is possible, especially where a seal is immediately adjacent into an edge of a package, that some of the energy will pass around the edge of the package or container, as is illustrated in dotted line 36 in FIG. 4. In order to prevent the interference of any wrap around energy with the receiving transducer, which could adversely affect a true reading of the integrity of the seal, with the present invention, the energy from the transmitting transducer may be otherwise focused and screened relative to the edge "E" of the package.

To prevent such wrap around energy from adversely affecting the receiving transducer and to maintain the package seal within the focal point between the transducers, a shield, head element or screen 40 may be mounted so as to engage and overlap the upper edge "E" of the package, which may be the pouch "P", as shown in FIG. 4. The screen 40 is shown as being carried within a fixed housing 41 spaced above the package conveyor "C". A spring or other resilient element 42 mounted within the housing allows the shield to be reciprocally movable along its elongated axis "A" depending upon the size and spacing of the edge "E" of the pouch "P" so that, in effect, the shield 40 can track along the edge of the pouch, thus compensating for any difference in edge configuration between one container and another. The shield 40 thus prevents any misdirected energy from being receivable by the receiving transducer 22.

Figure 6:
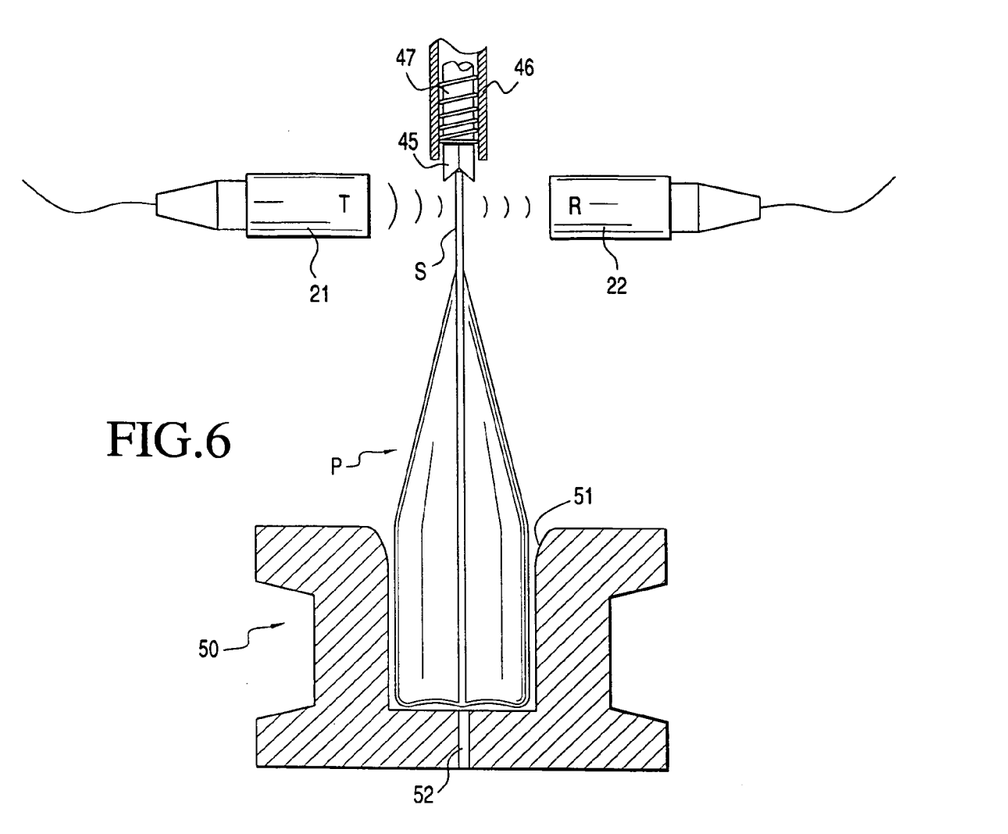
FIG. 6 is a cross sectional view of the pouch shown in the embodiment of FIG. 5 mounted within a carrier.
Figure 7:
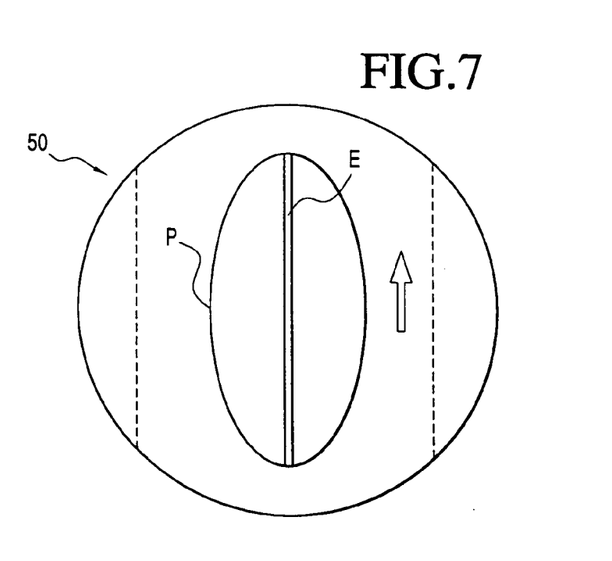
FIG. 7 is a top plan view of the embodiment of FIG. 6.

As opposed to the screen 40, a roller or wheel element 45 may be used to create a second barrier, as is shown in FIG. 6. The roller may also be resiliently mounted within a housing 46. A spring or other resilient member 47 provides sufficient force to cause the roller to positive track along the edge of a package.

Figure 5:
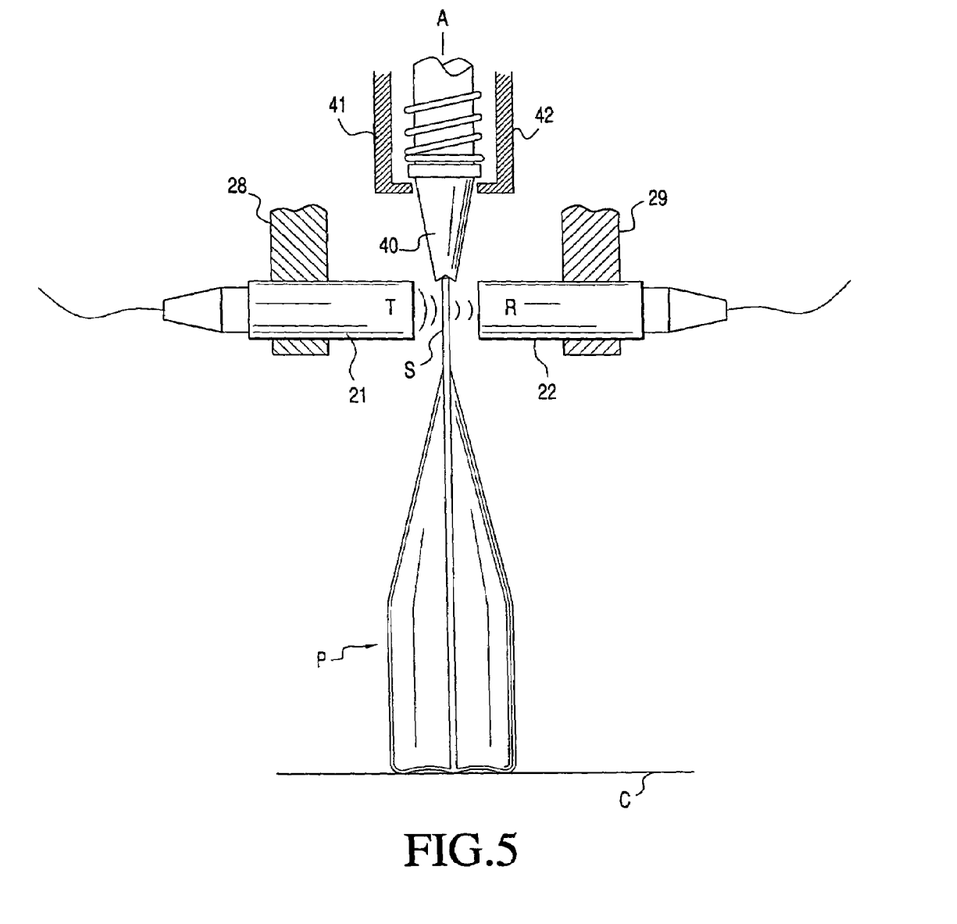
FIG. 5 is an alternate embodiment of the invention utilizing the transducer system generally shown in FIG. 1.

With further reference to FIG. 6, the pouch "P" shown in FIG. 5 is mounted within a carrier 50 having a slot or cavity 51 therein in which the pouch is selectively seated. The carrier may include a central opening 52 in the lower portion of the slot to allow drainage of fluids or other elements which may enter into the slot. The slot in the carrier is of a size to cradle a portion of the bottom of the pouch and thus stabilize the pouch as it passes through the testing station 20 so that the seal "S" is appropriately aligned between the transmitting transducer 21 and the receiving transducer 22.

Figure 8:
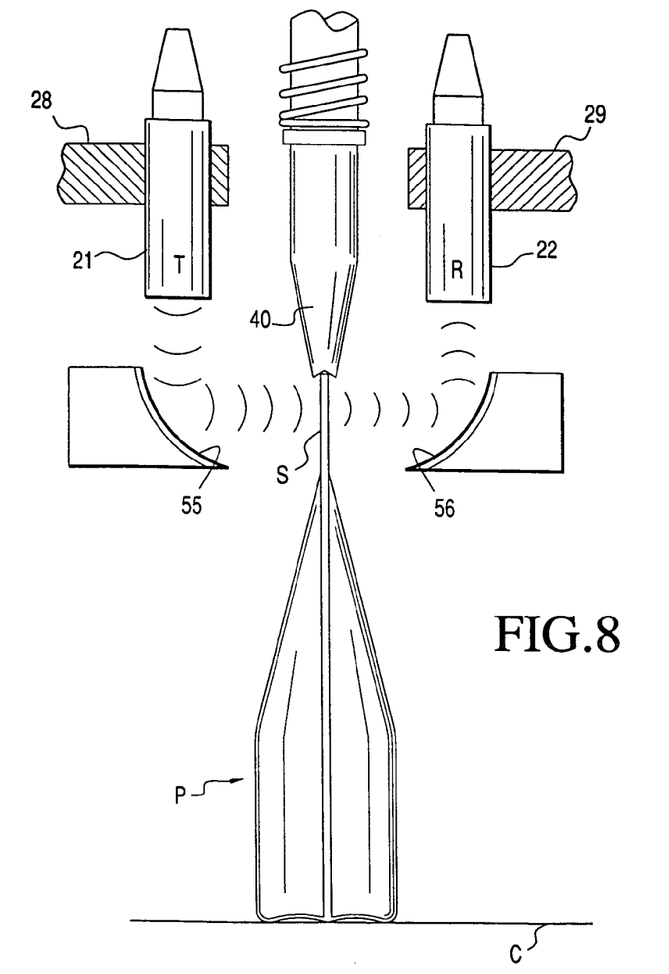
FIG. 8 is a side illustrational view of a variation of the embodiment shown in FIG. 5.

With specific reference to FIG. 8, a variation of the embodiment shown in FIG. 5 is disclosed wherein the transmitting transducer 21 is mounted generally parallel to the receiving transducer 22. In this embodiment, the supports 28 and 29 are mounted generally in line with one another on opposite sides of the shield 40. Energy from the transmitting receiver is directed towards a parabolic reflector surface 55 which directs the energy through the seal area "S" of the pouch "P". The energy passes through the seal and is directed by parabolic reflective surface 56 to the receiving transducer 22. The parabolic reflective surfaces can be utilized to effectively aim or direct the energy between the transmitting and receiving transducers.

Figure 9:
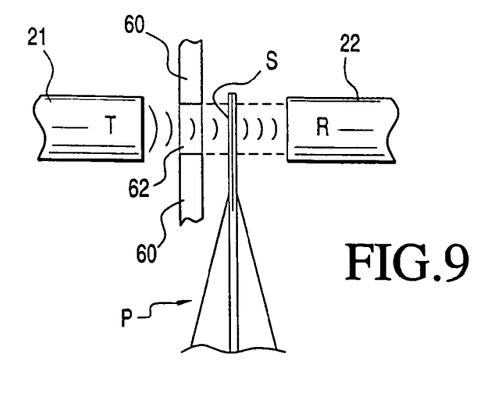
FIG. 9 is a partial illustrational view showing a further variation of the embodiment of FIG. 9 for focusing energy between the transmitting and receiving transducers.

With reference to FIG. 9 a further method of shielding or preventing wrap around energy from reaching the receiving transducer is disclosed. In this embodiment, a barrier plate 60 is mounted between the seal area "S" of the pouch "P" such that all energy issuing from the transmitting transducer 21 must pass through a circular or other shape of opening 62 formed in the barrier plate. The opening 62 will focus the ultrasonic energy directly through the seal area "S" and prevent any wrap around energy from reaching the receiving transducer 22.

Figure 10:
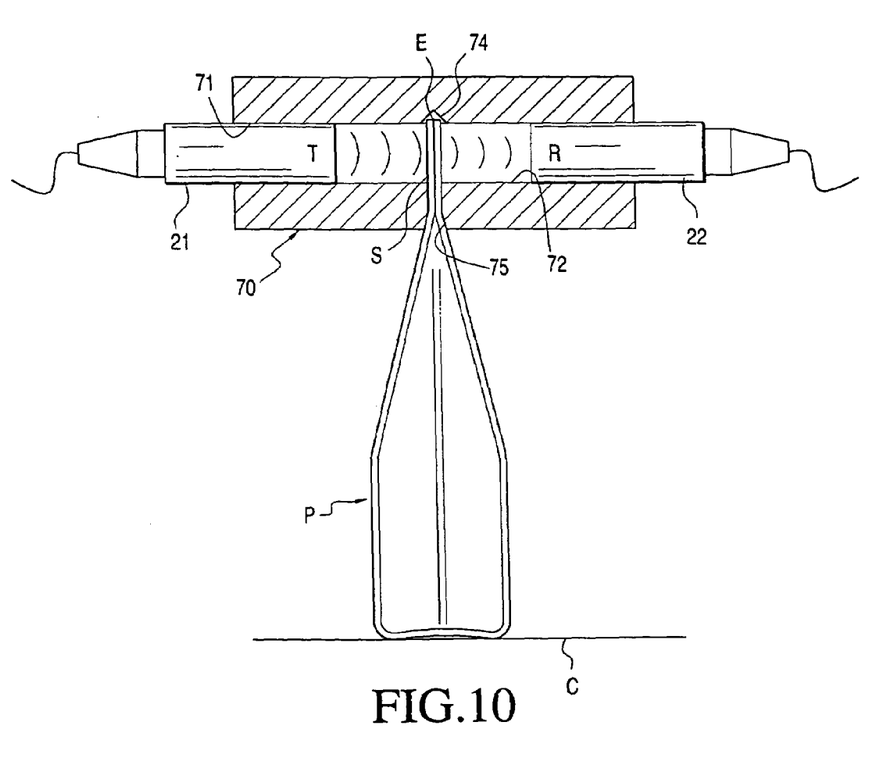
FIG. 10 is a cross sectional view of another embodiment of the invention.

With reference to FIG. 10, another variation of the embodiment of the invention shown in FIG. 5 is disclosed. In this embodiment, wrap around energy is prevented from reaching the receiving transducer 22 by providing a generally stationary guide channel housing 70 which is positioned above the conveyor "C" on which the pouch "P" is carried. The housing includes opposite aligned openings 71 and 72 in which the transmitting transducer 21 and the receiving transducer are mounted so as to be in open communication with one another. The space between the transducers permits ultrasonic energy to pass through air or other gaseous medium from the transmitting transducer toward the receiving transducer. The guide channel further includes an upper groove 74 in which the upper edge of the pouch is received such that no sound waves pass around the upper edge which would effect the amount of energy being received by the receiving transducer 22. Therefore, all ultrasonic energy must pass through the seal "IS". As shown, the housing also includes an open slot 75 in which the upper portion of the pouch is guided as it passes through the channel housing 70. As opposed to the fixed slot or groove 74 in the embodiment in FIG. 10, a resiliently mounted member, such as shown at 40 in the embodiment in FIG. 5, or a roller, as shown at 45 of FIG. 6, can be used and mounted within the housing 70.

Figure 11:
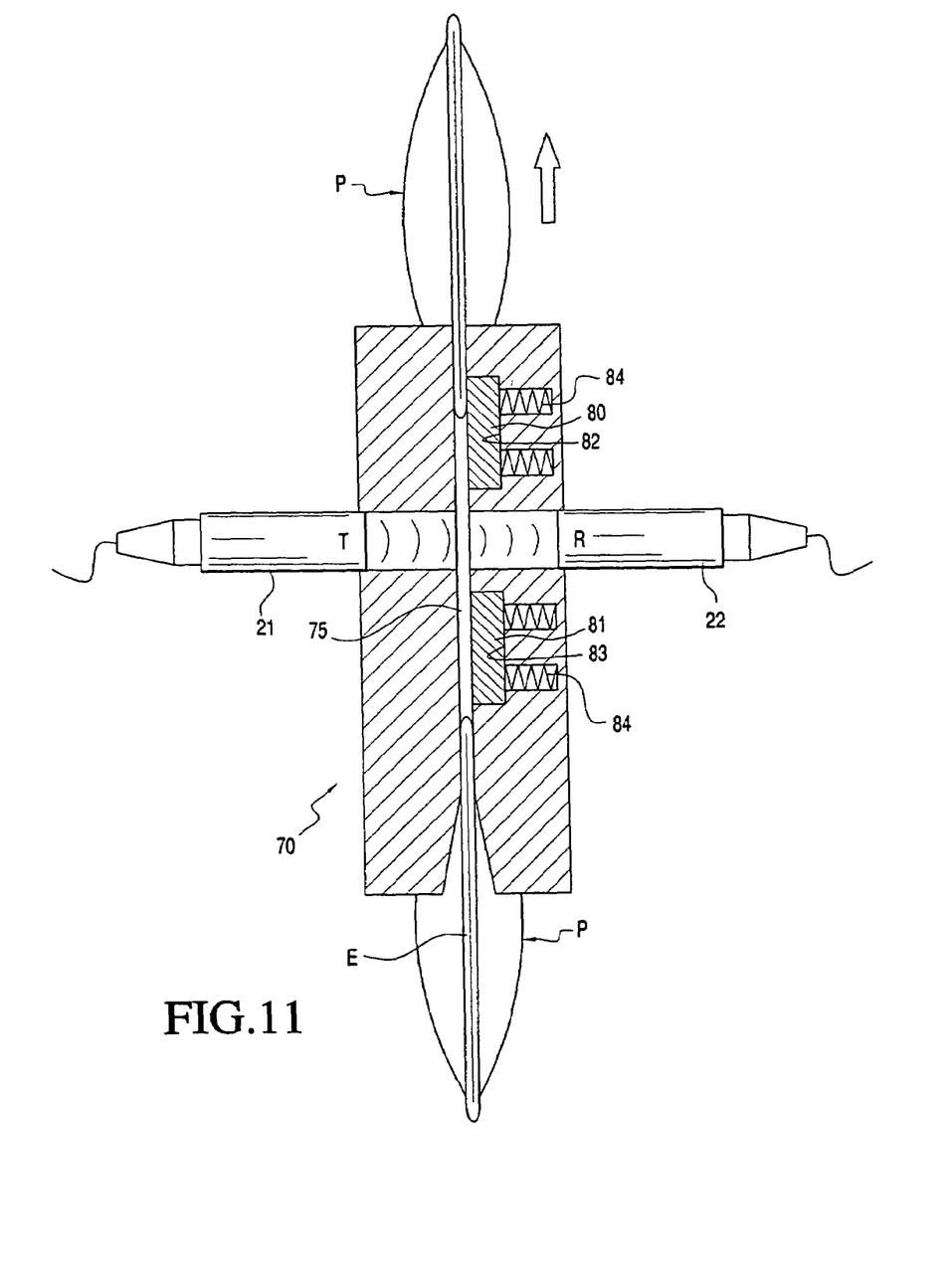
FIG. 11 is a cross sectional view taken from the top of the embodiment of FIG. 10 showing a variation for guiding a pouch relative thereto.

With specific reference to FIG. 11, a top cross sectional view of an embodiment, similar to that disclosed in FIG. 10, is shown wherein the housing 70 includes a pair of guide members 80 and 81 which are mounted within cavities 82 and 83, respectively, of the housing and which are resiliently urged by springs 84 toward the slot 75 and the upper edge of the pouch "P". The spring loaded guides serve to orient and properly position the upper edge of the pouch such that the seal is aligned between the transmitting transducer 21 and the receiving transducer 22. As shown in FIG. 11, the pouches are carried by an appropriate conveying device so as to pass sequentially through the testing device.

Figure 12:
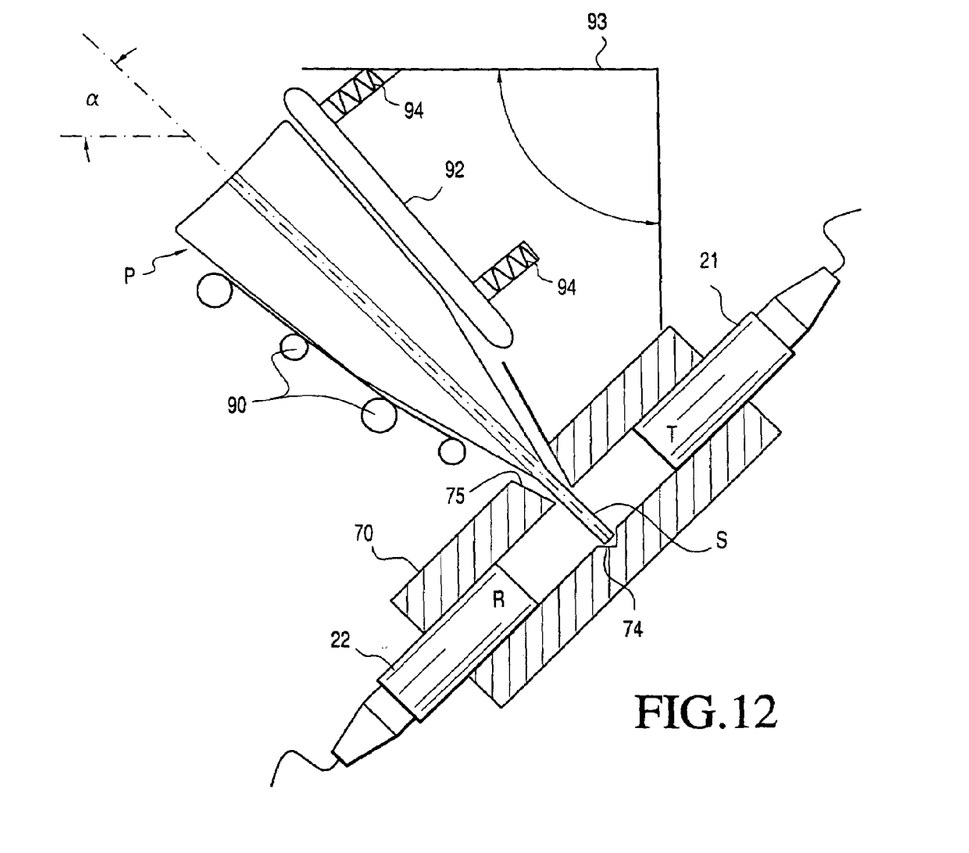
FIG. 12 is a cross sectional view of a further variation of the embodiment shown in FIG. 10.

A variation of the embodiment shown in FIGS. 10 and 11 is shown in FIG. 12. In this embodiment, the pouch "P" is being carried by a conveyor belt system 90 which is positioned at an angle with respect to horizontal, as shown at a. The housing 70 for mounting the transmitting and receiving transducers 21 and 22 is also mounted at an angle such that the edge "E" of the pouch engages within the slot or groove 74 which serves to prevent wrapping of energy between the transmitter and receiver.

In this embodiment, the pouch is guided and further stabilized by a plate 92 which may be resiliently urged by springs 94 towards the pouch. The plate is mounted withing a housing 93. The plate 92 insures that the pouch is positively guided and properly aligned as it passes through the channel housing 70 so as to insure that the seal area "S" of the pouch is properly aligned between the transmitting transducer and the receiving transducer.

Figure 13:
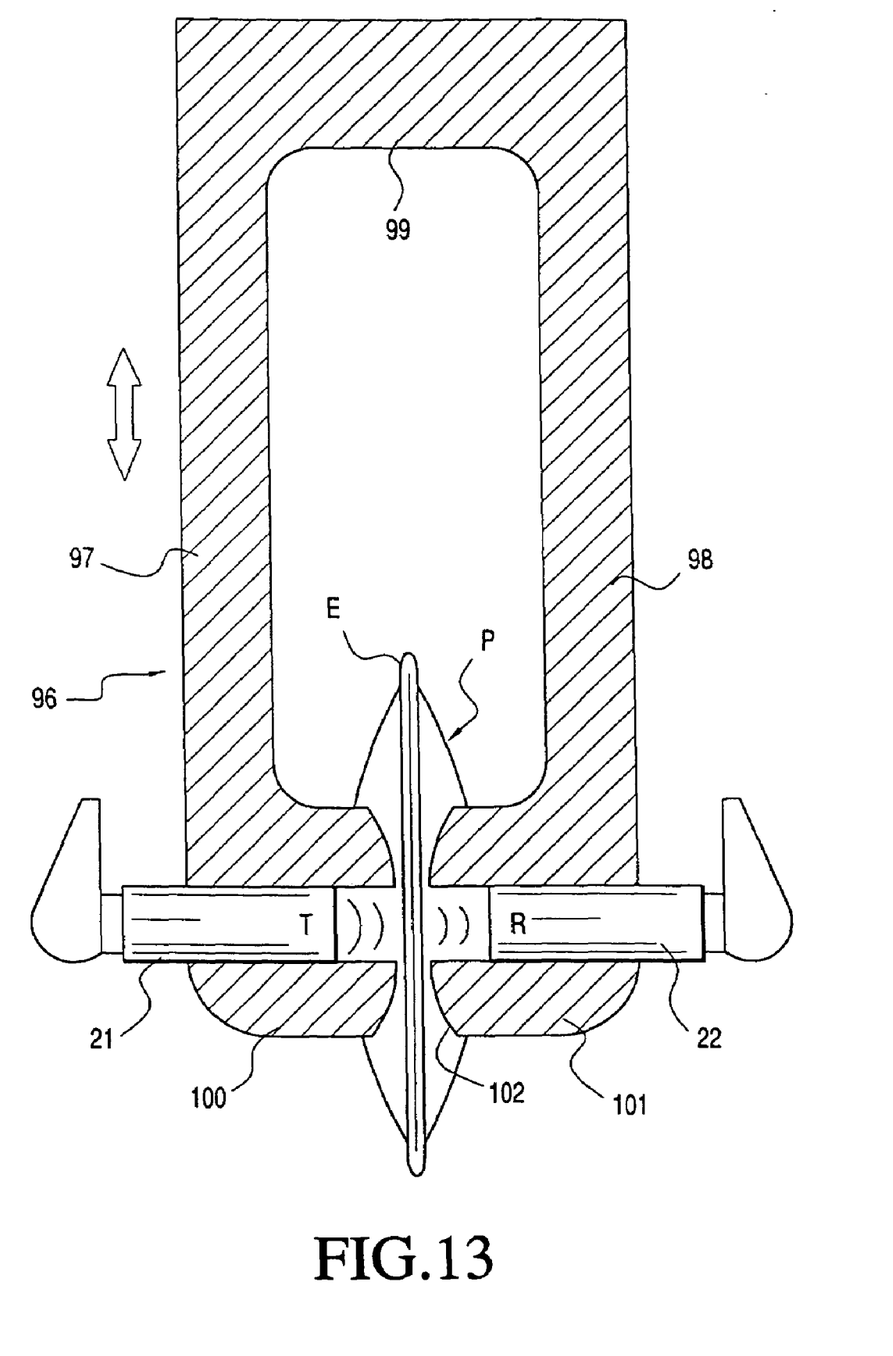
FIG. 13 is a variation of the embodiment of the invention shown in FIG. 1 shown in cross section.

A further embodiment of the invention is shown in FIG. 13, which is similar to that shown in FIG. 1. In this embodiment, the transmitting transducer and receiving transducer are mounted to a common support 96 which is generally formed in a u-shape including opposite parallel legs 97 and 98 which extend from a common base 99. Opposite the base 99, the support includes aligned arm segments 100 and 101 which are spaced relative to one another so as to define a guide channel 102 therebetween through which the seal and upper edge of a package extends as the seal area passes between the transmitting transducer and the receiving transducer 22. Although only one set of transducers is shown in the drawing figure, it is possible that several sets may be carried by a common support. Further, the support 96 may be carried by a separate conveying device such that the support moves relative to the package or pouch rather than the pouch moving relative to the testing transducers.

Further although not shown in FIG. 13, an appropriate shield could also be provided to prevent energy from passing over the edge of the package, as previously described with respect to the other embodiments of the invention.

Figure 14:
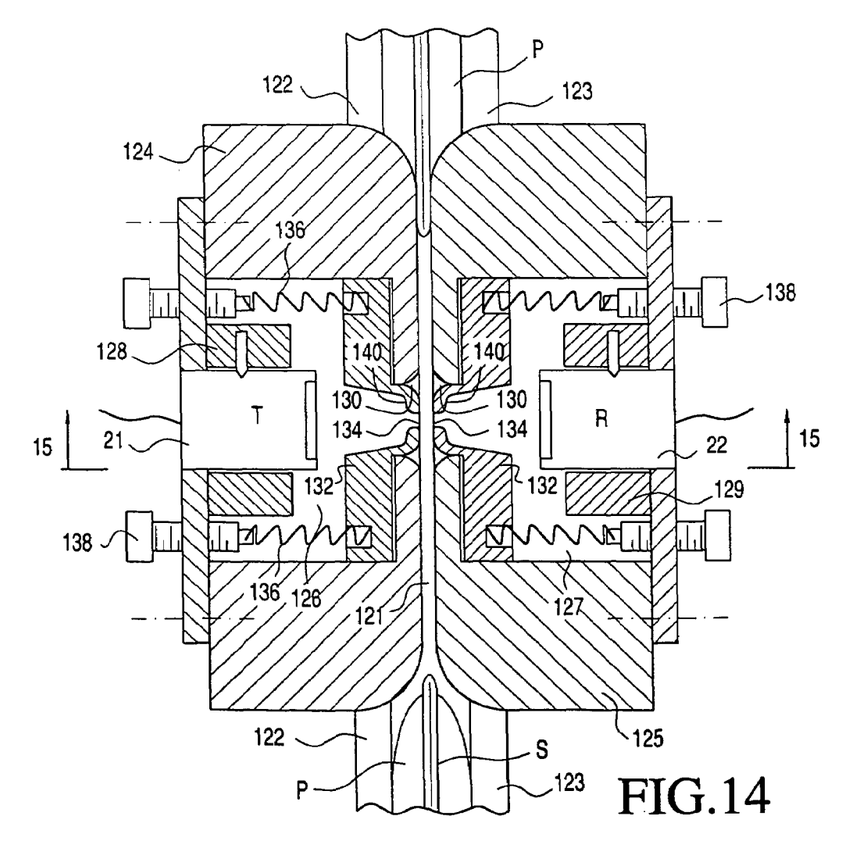
FIG. 14 is a partial cross-sectional view taken through an ultrasonic inspection head wherein energy from the transmitting transducer is focused toward a seal and a receiving transducer through adjustable focal plates.
Figure 15:
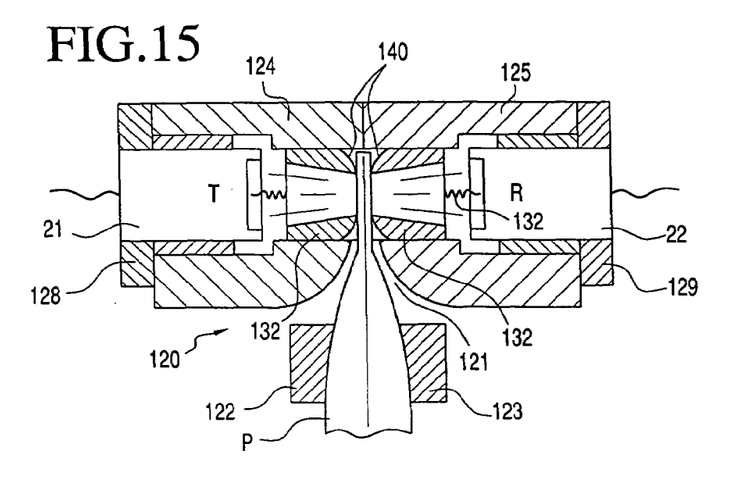
FIG. 15 is a cross-sectional view taken along line 15—15 of FIG. 14.

With particular reference to FIGS. 14 and 15, another variation of inspection station is shown. In this embodiment, the packages or pouches "P" are not only carried on a conveyor as previously described, they are also positively guided and aligned relative to a passage 121 in an inspection head 120 by opposing side conveyors 122 and 123. The inspection head includes two sections 124 and 125 each having a cavity 126 and 127 therein, respectively. The cavities are closed by transducer mounting plates 128 and 129 in which one or more transmitting transducers 21 and receiving transducers 22 are adjustably mounted. However, the cavities are in communication through openings 130 in the sections 124 and 125.

In the present embodiment, the ultrasonic energy is focused toward the seal area "S" of the packages as the edge of the package is guided within the slot or passage 121. Focusing is provided by adjustable elements 132 having focal openings 134 therein. Energy from the transmitting transducer is guided through the focal openings and thus prevents sound waves from being misdirected toward the receiving transducer. Further, the focal elements 132 may be resiliently movable by springs or like devices 136 so as to be automatically adjusted for different package sizes or thicknesses adjacent the package seals. Also, the force provided by the springs can be adjusted by screws or other adjustment members 138. In this embodiment, protruding portions 140 of the focal elements may contact the surface of the packages adjacent the seals as shown in the drawing figures.

Figure 16:
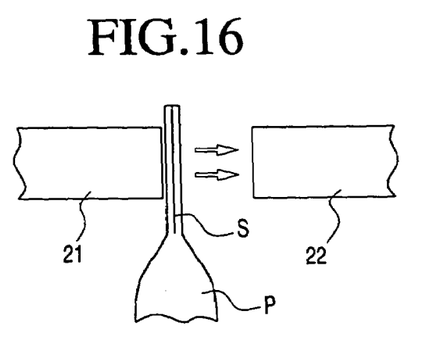
FIG. 16 is a partial side illustrational view of an embodiment of the invention in which a transmitting transducer is in contact with a package adjacent to a seal with the receiving transducer being in spaced relationship from the seal in a gaseous environment.

With respect to FIG. 16, a variation of the non-contact airborne ultrasonic testing systems previously disclosed is shown. In the embodiment of FIG. 16, the transmitting transducer 21 is showing as being in contact with the pouch "P" adjacent to the seal area "S" during the testing. Ultrasonic energy which passes through the seal area is received by the receiving transducer 22 which is spaced at a distance from the seal in a gaseous environment, such as ambient air.

Figure 17:
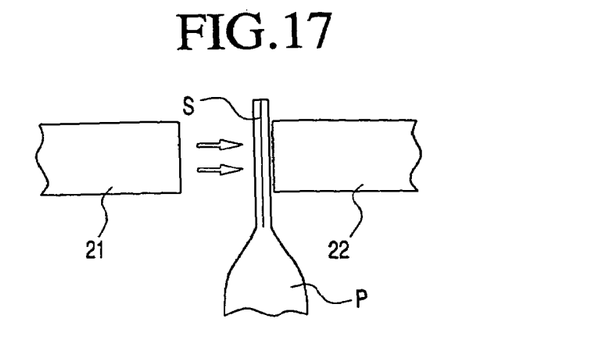
FIG. 17 is a view similar to FIG. 14 except showing the receiving transducer in surface contact with a package or pouch adjacent to a seal area wherein ultrasonic energy is transmitted from a transmitting transducer spaced from the package.

FIG. 17 is a variation of contact airborne ultrasonic testing or inspecting in accordance with the present invention wherein the receiving transducer 22 is shown as being in contact with the package or pouch "P" adjacent to the seal "S". Ultrasonic energy is transmitted toward the seal area by a transmitting transducer 21 which is spaced in non-contact relationship with respect to the package or pouch.

Figure 18:
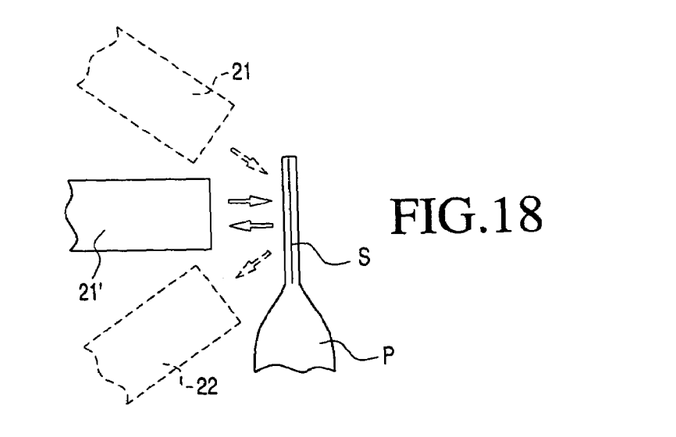
FIG. 18 is an illustrational view of another embodiment of the invention wherein, in solid line, a single transducer element is utilized as a transmitting and a receiving transducer in accordance with the invention and wherein, in dotted line, a transmitting transducer and receiving transducer are shown being oriented on the same side of a seal being inspected.

A further variation of the present invention is disclosed in solid line in FIG. 18 wherein a transmitting transducer 21' also functions as a receiving transducer. In this embodiment, ultrasonic energy from the transmitting transducer 21' is directed at the seal area "S" of the package "P". Such energy is reflected and subsequently detected by the transmitting transducer which is electrically controlled to also function as a receiving transducer to record the amount of reflected energy from the seal area "S". This type of system would generally be described as a pulse-echo type system.

A variation of pulse-echo system is shown in dotted line in FIG. 18 wherein the transmitting transducer 21 is mounted so as to direct ultrasonic energy toward the seal area "S" with energy being reflected and detected by the receiving transducer 22 which is mounted on the same side of the seal area as the transmitting transducer.

Figure 19:
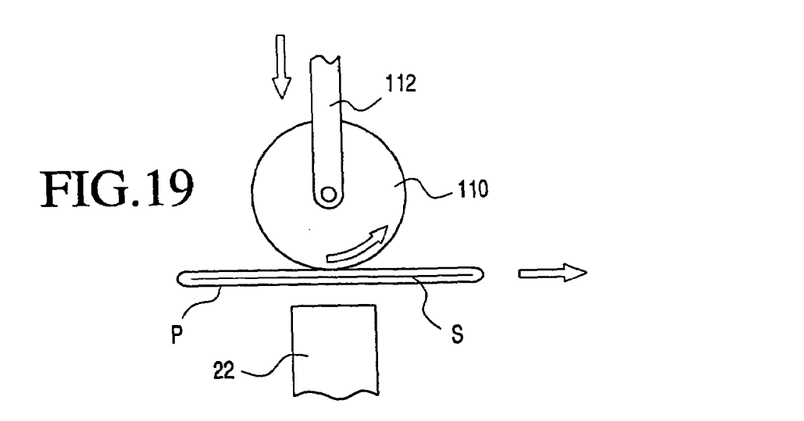
FIG. 19 is a partial side illustrational view of another embodiment of the invention wherein the transmitting transducer is shown as being a rolling element capable of tracking along a package adjacent to a seal area.

A further variation of the present invention is shown in FIG. 19. In this variation, the transmitting transducer is movable and is formed as a rotatable wheel 110 mounted to a support assembly 112. The wheel is allowed to roll along a portion of the package "P" adjacent to the seal area "S" during testing or inspecting with the amount of acoustic energy passing through the seal area being detected by the receiving transducer 22. Although not shown in the drawings, the receiving transducer may also be formed as a wheel-like element similar to that as shown at 110.

The foregoing description of the preferred embodiment of the invention has been presented to illustrate the principles of the invention and not to limit the invention to the particular embodiment illustrated. It is intended that the scope of the invention be defined by all of the embodiments encompassed within the following claims and their equivalents.

I claim:

1. An apparatus for inspecting a seal of a package in a gaseous environment wherein the apparatus includes at least one airborne ultrasonic system including at least one airborne ultrasonic transmitting transducer spaced from at least one airborne ultrasonic receiving transducer, means for moving a package or said at least one airborne ultrasonic transmitting transducer relative to one another such that ultrasonic energy from said at least one airborne ultrasonic transducer passes through a seal of the package before being received by said at least one airborne ultrasonic receiving transducer, analyzer means for receiving signals from said at least one airborne ultrasonic receiving transducer for providing an indication of integrity of the seal, and means for preventing ultrasonic energy from passing about the edge of the package adjacent the seal such that said at least one airborne ultrasonic receiving transducer receives only ultrasonic energy passing through the seal from said at least one airborne ultrasonic transmitting transducer.

2. The apparatus of claim 1 including means for focusing ultrasonic energy from said at least one airborne ultrasonic transmitting transducer toward said at least one airborne ultrasonic receiving transducer.

3. The apparatus of claim 2 wherein said means for focusing includes a sound screen positioned intermediate said at least one airborne ultrasonic transmitting transducer and said at least one airborne ultrasonic receiving transducer and an opening in said sound screen to permit ultrasonic energy to pass therethrough.

4. The apparatus of claim 1 wherein said means for preventing ultrasonic energy from passing about the edge of the packages adjacent the seal includes a screen element for engaging the edge of the package adjacent the seal.

5. The apparatus of claim 4 including resilient means for urging said screen element into engagement with the edge of the package.

6. The apparatus of claim 5 wherein said screen element is in a form of a roller.

7. The apparatus of claim 1 including first reflecting means for reflecting ultrasonic energy from said at least one airborne ultrasonic transmitting transducer toward the seal and a second reflecting means for reflecting ultrasonic energy passing through the seal toward said at least one airborne ultrasonic receiving transducer.

8. The apparatus of claims 2 wherein said means for focusing includes a guide housing having opposing side portions in which said at least one airborne ultrasonic transmitting transducer and at least one airborne ultrasonic receiving transducer are mounted so as to be on opposite sides of a central passage through which the seal passes.

9. The apparatus of claim 8 wherein said means for preventing ultrasonic energy from passing about the edge of the package adjacent the seal includes a groove in said guide housing for providing a seal for the edge of the package.

10. The apparatus of claim 9 including resiliently mounted guide means mounted to said guide housing for guidingly positioning the edge of the package within said central passage.

11. The apparatus of claim 8 wherein said means for focusing further includes adjustable elements having focal openings therein mounted in each of said side portions of said guide housing and spaced in opposing relationship intermediate said at least one airborne ultrasonic transmitting transducer and at least one airborne ultrasonic receiving transducer.

12. The apparatus of claim 11 wherein said means for moving includes a conveyor system on which the package may be carried and means for resiliently urging the package against said conveyor system.

13. The apparatus of claim 1 wherein said means for moving includes a conveyor for supporting the package and conveying the package relative to said at least one airborne ultrasonic transmitting transducer and said at least one airborne ultrasonic receiving transducer.

14. The apparatus of claim 13 including means for resiliently urging the package against said conveyor.

15. The apparatus of claim 1 wherein said means for moving includes a rotatable support for rotating the package relative to the at least one airborne ultrasonic transmitting transducer and said at least one airborne ultrasonic receiving transducer.

16. The apparatus of claim 15 wherein said rotatable support forms a portion of a conveyor system.

17. The apparatus of claim 1 wherein said means for moving includes at least one movable support for carrying said at least one airborne ultrasonic transmitting transducer and said at least one airborne ultrasonic receiving transducer.

18. The apparatus of claim 17 wherein said at least one support includes spaced leg segments having spaced and aligned arm portions to which said at least one airborne ultrasonic transmitting transducer and said at least one airborne ultrasonic receiving transducer are mounted so as to be in opposing relationship with one another.

* * * * *